(12) United States Patent
Tomiyori et al.

(10) Patent No.: US 10,384,992 B2
(45) Date of Patent: Aug. 20, 2019

(54) MANUFACTURING METHOD OF HYDROFLUOROOLEFIN

(71) Applicant: AGC Inc., Chiyoda-ku (JP)

(72) Inventors: Yusuke Tomiyori, Chiyoda-ku (JP); Masahiko Nakamura, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 0 days.

(21) Appl. No.: 15/725,886

(22) Filed: Oct. 5, 2017

(65) Prior Publication Data

US 2018/0037524 A1     Feb. 8, 2018

Related U.S. Application Data

(63) Continuation of application No. PCT/JP2016/061560, filed on Apr. 8, 2016.

(30) Foreign Application Priority Data

Apr. 9, 2015    (JP) ................................ 2015-080022

(51) Int. Cl.
     *C07C 17/25*          (2006.01)
     *C07C 21/18*          (2006.01)

(52) U.S. Cl.
     CPC .............. *C07C 17/25* (2013.01); *C07C 21/18* (2013.01)

(58) Field of Classification Search
     CPC ...................................................... C07C 17/25
     See application file for complete search history.

(56) References Cited

U.S. PATENT DOCUMENTS

| | | |
|---|---|---|
| 5,856,593 A | 1/1999 | Powell et al. |
| 5,905,177 A | 5/1999 | Seo et al. |
| | (Continued) | |

FOREIGN PATENT DOCUMENTS

| | | |
|---|---|---|
| CA | 2019914 | 1/1991 |
| CN | 1254329 A | 5/2000 |
| | (Continued) | |

OTHER PUBLICATIONS

Jung, J. et al. "Advanced CO2 Capture process using MEA scrubbing: Configuration of a Split Flow and Phase Separation Heat Exchanger" Energy Procedia 37 (2013) 1778-1784 (Year: 2013).*

(Continued)

*Primary Examiner* — Medhanit W Bahta
(74) *Attorney, Agent, or Firm* — Oblon, McClelland, Maier & Neustadt, L.L.P.

(57) ABSTRACT

A method for manufacturing hydrofluoroolefin, includes: converting hydrofluorocarbon represented by a formula (1) into hydrofluoroolefin (HFO) represented by formula (2) in the presence of carbon dioxide to obtain a first gas composition containing hydrofluoroolefin and carbon dioxide; and separating carbon dioxide contained in the first gas composition to obtain a second gas composition containing HFO, $CR^1R^2X^1CR^3R^4X^2 \ldots (1)$, $CR^1R^2{=}CR^3R^4 \ldots (2)$, wherein $R^1$ to $R^3$ are each independently hydrogen atom or fluorine atom, $R^4$ is hydrogen atom, fluorine atom, $CH_3$, $CH_2F$, $CHF_2$ or $CF_3$, the total number of fluorine atoms of $R^1$ to $R^4$ is one or more, and the total number of hydrogen atoms of $R^1$ to $R^4$ is one or more, $X^1$ and $X^2$ are each hydrogen atom or fluorine atom where $X^2$ is the fluorine atom when $X^1$ is the hydrogen atom, and $X^2$ is the hydrogen atom when $X^1$ is the fluorine atom.

10 Claims, 1 Drawing Sheet

(56) References Cited

U.S. PATENT DOCUMENTS

| | | | |
|---|---|---|---|
| 6,156,097 A | 12/2000 | O'Brien et al. | |
| 2010/0185029 A1* | 7/2010 | Elsheikh | C07C 17/206 570/157 |

FOREIGN PATENT DOCUMENTS

| | | |
|---|---|---|
| DE | 690 12 891 T2 | 3/1995 |
| DE | 696 02 880 T2 | 10/1999 |
| DE | 698 32 182 T2 | 4/2005 |
| EP | 0 406 748 A2 | 1/1991 |
| EP | 0 738 699 A1 | 10/1996 |
| JP | 3-115234 | 5/1991 |
| JP | 8-291086 | 11/1996 |
| JP | 10-505337 | 5/1998 |
| JP | 2001-526655 | 12/2001 |
| JP | 2008-115191 | 5/2008 |
| WO | WO 98/50331 A1 | 11/1998 |

OTHER PUBLICATIONS

Mahmoudkhani, M. et al. "Low-energy sodium hydroxide recovery for CO2 capture from atmospheric air—Thermodynamic analysis" International Journal of Greenhouse Gas Control 3 (2009) 376-384 (Year: 2009).*

International Search Report dated Jul. 5, 2016 in PCT/JP2016/061560, filed on Apr. 8, 2016 (with English Translation).

Written Opinion dated Jul. 5, 2016 in PCT/JP2016/061560, filed on Apr. 8, 2016.

* cited by examiner

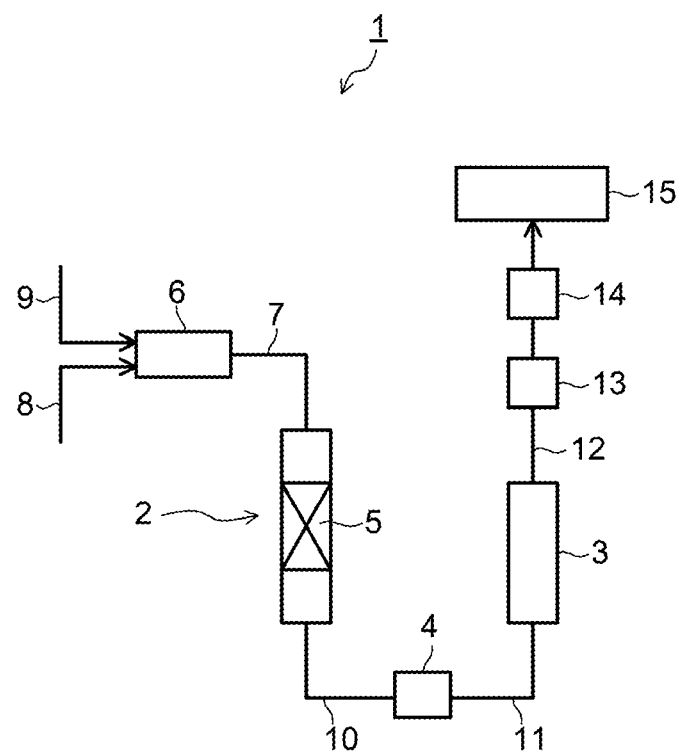

MANUFACTURING METHOD OF HYDROFLUOROOLEFIN

CROSS-REFERENCE TO RELATED APPLICATIONS

This application is a continuation of prior International Application No. PCT/JP2016/061560, filed on Apr. 8, 2016 which is based upon and claims the benefit of priority from Japanese Patent Application No. 2015-080022, filed on Apr. 9, 2015; the entire contents of all of which are incorporated herein by reference.

FIELD

The present invention relates to a manufacturing method of hydrofluoroolefin, particularly to a method efficiently manufacturing hydrofluoroolefin from hydrofluorocarbon.

BACKGROUND

In this specification, abbreviated names of halogenated hydrocarbon compounds are described in parentheses after the compound names, and in this specification, the abbreviated names are employed in place of the compound names as necessary.

In recent years, since hydrofluoroolefin such as trifluoroethylene (HFO-1123) and 2,3,3,3-tetrafluoropropene (HFO-1234yf) has a small global warming potential (GWP), it is largely expected as a new refrigerant taking the place of difluoromethane (HFC-32) and 1,1,1,2,2-pentafluoroethane (HFC-125) being greenhouse effect gas.

Conventionally, there has been known a method using 1,1,1,2-tetrafluoroethane (HFC-134a) which is relatively inexpensive as a raw material, as a manufacturing method of HFO-1123. Besides, there has been known a method using 1,1,1,2,2-pentafluoropropane (HFC-245cb) or 1,1,1,2,3-pentafluoropropane (HFC-245eb) as a raw material, as a manufacturing method of HFO-1234yf.

For example, there is disclosed a method manufacturing HFO-1123 by dehydrofluorination reaction of HFC-134a while using metal fluoride or metal oxide as a catalyst in JP-A Hei 10-505337 (Patent Document 1). In the manufacturing method disclosed in Patent Document 1, HFC-134a being a raw material and source gas containing nitrogen as diluent gas are supplied to a heating reaction zone, then the dehydrofluorination reaction of HFC-134a is set off in the presence of catalyst in the heating reaction zone to thereby manufacture a composition containing HFO-1123.

SUMMARY

However, in the manufacturing method disclosed in Patent Document 1, there are contained HFO-1123 and nitrogen which is the diluent gas of HFC-134a being the raw material, in the composition. A boiling point of HFO-1123 is low, and therefore, severe conditions of low-temperature and high-pressure become necessary to separate HFO-1123 and nitrogen in the composition. Accordingly, equipment enabling a low-temperature and high-pressure state in a reactor is necessary so as to separate HFO-1123 and nitrogen after the reaction, when nitrogen is used as the diluent gas. Further, the equipment as stated above results in high manufacturing cost such as an electric bill.

A problem to be solved by the present invention is to provide a manufacturing method of hydrofluoroolefin capable of easily separating hydrofluoroolefin and diluent gas even when a boiling point of hydrofluoroolefin is low, and excellent in productivity.

The present invention provides a manufacturing method of hydrofluoroolefin having a constitution described in the following [1] to [12].

[1] A manufacturing method of hydrofluoroolefin, including:

a step obtaining a first gas composition containing hydrofluoroolefin and carbon dioxide by converting hydrofluorocarbon represented by the following formula (1) into the hydrofluoroolefin represented by the following formula (2) in the presence of the carbon dioxide; and a step obtaining a second gas composition containing the hydrofluoroolefin by separating the carbon dioxide contained in the first gas composition, $$CR^1R^2X^1CR^3R^4X^2 \quad (1)$$

$$CR^1R^2{=}CR^3R^4 \quad (2)$$

wherein $R^1$ to $R^3$ in the formula (1) and the formula (2) are each independently a hydrogen atom or a fluorine atom, $R^4$ is a hydrogen atom, a fluorine atom, $CH_3$, $CH_2F$, $CHF_2$ or $CF_3$, the total number of fluorine atoms of $R^1$ to $R^4$ is one or more, and the total number of hydrogen atoms of $R^1$ to $R^4$ is one or more, $X^1$ and $X^2$ are each a hydrogen atom or a fluorine atom, $X^2$ is the fluorine atom when $X^1$ is the hydrogen atom, and $X^2$ is the hydrogen atom when $X^1$ is the fluorine atom.

[2] The manufacturing method of hydrofluoroolefin according to [1], wherein the process obtaining the second gas composition includes a step bringing the first gas composition into contact with an alkaline solution.

[3] The manufacturing method of hydrofluoroolefin according to [2], wherein the alkaline solution contains an inorganic base or an organic base where pKa of conjugate acid is six or more.

[4] The manufacturing method of hydrofluoroolefin according to [3], wherein the inorganic base is at least one kind of base selected from a group consisting of sodium hydroxide, potassium hydroxide, potassium carbonate and calcium oxide.

[5] The manufacturing method of hydrofluoroolefin according to [3], wherein the organic base is at least one kind of base selected from a group consisting of triethylamine, tributylamine, monoethanolamine, n-propanolamine and N-methyldiethanolamine.

[6] The manufacturing method of hydrofluoroolefin according to any one of [1] to [5], wherein a molar ratio between the hydrofluorocarbon and the carbon dioxide in the step obtaining the first gas composition (hydrofluorocarbon/carbon dioxide) is 0.3/99.7 or more and 99.5/0.5 or less.

[7] The manufacturing method of hydrofluoroolefin according to any one of [1] to [6], wherein the hydrofluorocarbon is HFC-134a, and the hydrofluoroolefin is HFO-1123.

[8] The manufacturing method of hydrofluoroolefin according to any one of [1] to [6], wherein the hydrofluorocarbon is HFC-245cb and/or HFC-245eb, and the hydrofluoroolefin is HFO-1234yf.

[9] The manufacturing method of hydrofluoroolefin according to any one of [1] to [8], wherein the step obtaining the first gas composition includes a step bringing the hydrofluorocarbon into contact with a catalyst.

[10] The manufacturing method of hydrofluoroolefin according to [9], wherein the catalyst is at least one kind of substance selected from a group consisting of metal, metal oxide and metal halide.

[11] The manufacturing method of hydrofluoroolefin according to [9] or [10], wherein the catalyst is at least one kind of substance selected from a group consisting of cobalt, nickel, palladium, chromium oxide, aluminum oxide, zinc oxide, iron fluoride, aluminum fluoride, aluminum chloride, chromium fluoride, chromium chloride and silicon oxide.

[12] The manufacturing method of hydrofluoroolefin according to any one of [1] to [11], wherein in the step obtaining the first gas composition, a temperature to convert the hydrofluorocarbon into the hydrofluoroolefin is 200° C. or more and 1200° C. or less.

According to the present invention, it is possible to provide a manufacturing method of hydrofluoroolefin capable of easily separating hydrofluoroolefin and diluent gas of hydrofluorocarbon being a raw material, even when a boiling point of hydrofluoroolefin is low, and excellent in productivity.

BRIEF DESCRIPTION OF THE DRAWINGS

The FIGURE is a schematic view illustrating an example of a reaction device used for a manufacturing method of hydrofluoroolefin according to the present invention.

DETAILED DESCRIPTION

Hereinafter, embodiments of the present invention are described.

A manufacturing method of hydrofluoroolefin of the present invention includes the following step (I) and step (II).

Step (I): A reaction step obtaining a first gas composition containing hydrofluoroolefin and carbon dioxide by converting at least one kind of hydrofluorocarbon represented by a formula (1) into hydrofluoroolefin represented by a formula (2) in the presence of carbon dioxide.

Step (II): A separation step obtaining a second gas composition containing hydrofluoroolefin by separating carbon dioxide contained in the first gas composition.

The formula (1) is $CR^1R^2X^1CR^3R^4X^2$, and the formula (2) is $CR^1R^2\!=\!CR^3R^4$. Besides, in the formula (1) and formula (2), $R^1$ to $R^3$ are each independently a hydrogen atom or a fluorine atom, $R^4$ is a hydrogen atom, a fluorine atom, $CH_3$, $CH_2F$, $CHF_2$ or $CF_3$, the total number of fluorine atoms of $R^1$ to $R^4$ is one or more, and the total number of hydrogen atoms of $R^1$ to $R^4$ is one or more. $X^1$ and $X^2$ are each a hydrogen atom or a fluorine atom, where $X^2$ is the fluorine atom when $X^1$ is the hydrogen atom, and $X^2$ is the hydrogen atom when $X^1$ is the fluorine atom.

In the step (I), a reaction where the hydrofluoroolefin represented by the formula (2) is generated from the hydrofluorocarbon represented by the formula (1) can be represented by the following reaction formula (3).

[Chemical Formula 1]

$$\underset{\text{Formula (1)}}{R^1\underset{X^1}{\overset{R^2}{\!\!\!\!\!\!\diagup\!\!\!\!\!\!\diagdown}}\underset{X^2}{\overset{R^3}{\!\!\!\!\!\!\diagup\!\!\!\!\!\!\diagdown}}R^4} \rightleftharpoons \underset{\text{Formula (2)}}{R^1\underset{R^1}{\overset{R^2}{\!\!\!\diagdown}}\!\!=\!\!\underset{R^4}{\overset{R^3}{\!\!\!\diagup}}} + HF \qquad \text{Formula (3)}$$

The hydrofluorocarbon represented by the formula (1) is properly processed under a predetermined condition, then a dehydrofluorination reaction where $X^1$ and $X^2$ of the hydrofluorocarbon represented by the formula (1) are simultaneously desorbed occurs. According to the dehydrofluorination reaction of hydrofluorocarbon represented by the reaction formula (3), the hydrofluoroolefin represented by the formula (2) and hydrogen fluoride are simultaneously generated.

In the manufacturing method of hydrofluoroolefin of the present invention, the numbers of carbons of the hydrofluorocarbon represented by the formula (1) and the hydrofluoroolefin represented by the formula (2) are each two to three.

In the manufacturing method of hydrofluoroolefin of the present invention, as a combination of the hydrofluorocarbon represented by the formula (1) being a raw material and the hydrofluoroolefin represented by the formula (2) being an object, there can be cited, for example, trifluoroethane (1,1,1-trifluoroethane (HFC-143a), 1,1,2-trifluoroethane (HFC-143), or a mixture of HFC-143a and HFC-143) and 1,1-difluoroethylene (HFO-1132a), tetrafluoroethane (1,1,2, 2-tetrafluoroethane (HFC-134), HFC-134a, or a mixture of HFC-134 and HFC-134a) and HFO-1123, pentafluoropropane (HFC-245cb, HFC-245eb, or a mixture of HFC-245cb and HFC-245eb) and HFO-1234yf, pentafluoropropane (1,1, 1,3,3-pentafluoropropane (HFC-245fa), HFC-245eb, or a mixture of HFC-245fa and HFC-245eb) and 1,3,3,3-tetrafluoropropene (HFO-1234ze) (trans-1,3,3,3-tetrafluoropropene (HFO-1234ze(E)), cis-1,3,3,3-tetrafluoropropene (HFO-1234ze(Z)), or a mixture of HFO-1234ze(E) and HFO-1234ze(Z)), and so on. Among them, it is preferable to manufacture HFO-1123 from HFC-134a, HFO-1234yf from pentafluoropropane (HFC-245cb, HFC-245eb, and the mixture of HFC-245cb and HFC-245eb) respectively from a point that the hydrofluoroolefin represented by the formula (2) can be efficiently manufactured. Note that in the specification, a compound name and an abbreviated name indicate to be E system and/or Z system when the compound name or the abbreviated name is described without making any mention. Besides, when (E) is added after the compound name or the abbreviated name, it means that the compound name or the abbreviated name is E system, and when (Z) is added after the compound name or the abbreviated name, it means that the compound name or the abbreviated name is Z system.

The manufacturing method of hydrofluoroolefin of this invention may be either an all continuous-type manufacturing method where the step (I) and the step (II) are continuously carried out, or may be an all batch-type manufacturing method where the step (I) and the step (II) are each a batch-type process, as long as the step (I) and the step (II) are carried out in this sequence.

Besides, the step (I) may be either a continuous step or a batch step. The step (II) may also be either a continuous step or a batch step as same as the step (I). The step (II) is preferably the continuous step from viewpoints of reducing time for maintenance and increasing productivity.

The manufacturing method of hydrofluoroolefin of this invention may further include a step separating hydrogen fluoride contained in the first gas composition (hereinafter, it is also referred to as a step (A)) between the step (I) and the step (II). Hydrogen fluoride generated by the reaction formula (3) is separated by the step (A), and thereby, it is possible to reduce loads on processes such as refining of the hydrofluoroolefin represented by the formula (2) as the object and recovering the hydrofluorocarbon represented by the formula (1), carbon dioxide, and so on, and productivity is improved.

When the manufacturing method of hydrofluoroolefin of this invention includes the step (A) in addition to the step (I) and the step (II), the manufacturing method may be the all continuous-type manufacturing method, the all batch-type manufacturing method, or a patrial continuous-type manufacturing method where a part of the steps among these steps is the batch-type step, and other steps are continuously carried out. The step (A) is preferably the continuous step from the viewpoints of reducing time for maintenance and increasing productivity.

Hereinafter, the step (I), the step (II), and the step (A) are further described.

<Step (I)>

In the step (I), the hydrofluorocarbon represented by the formula (1) in the source gas is converted into the hydrofluoroolefin represented by the formula (2) in the presence of carbon dioxide. The conversion from the hydrofluorocarbon represented by the formula (1) into the hydrofluoroolefin represented by the formula (2) is preferably carried out by bringing the hydrofluorocarbon represented by the formula (1) into contact with a catalyst. Hereinafter, a mode using the catalyst is described, but the step (I) in the manufacturing method of hydrofluoroolefin of this invention is not limited to such a mode.

(Source Gas)

The source gas contains the hydrofluorocarbon represented by the formula (1) being the raw material and the diluent gas of the hydrofluorocarbon. Further, the source gas may contain other compounds in addition to the hydrofluorocarbon represented by the formula (1) and the diluent gas in a range not damaging an effect of this invention. Besides, the source gas may be partially liquefied under high-pressure. The source gas is preferably gas composed of only the hydrofluorocarbon represented by the formula (1), or a gas component whose content ratio of the hydrofluorocarbon represented by the formula (1) is 50 mol % or more. Note that in the specification, the diluent gas means gas to dilute the raw material.

Note that the source gas may contain the hydrofluoroolefin represented by the formula (2). Accordingly, it is possible to use the second gas component obtained by various manufacturing methods of hydrofluoroolefin including the manufacturing method of hydrofluoroolefin of this invention as the source gas in the step (I) as long as the second gas component contains the hydrofluorocarbon represented by the formula (1) for 50 mol % or more.

Besides, regarding supply of the source gas containing the hydrofluorocarbon represented by the formula (1) as a reaction component to a reaction field (for example, a heated reactor), both of the source gas and the catalyst may be continuously supplied, or only one of the source gas and the catalyst may be continuously supplied, and the other may be supplied by batch when the step (I) is the continuous step. It is preferable that the catalyst is supplied to the reactor by batch, and thereafter, the source gas containing the hydrofluorocarbon represented by the formula (1) is continuously supplied to the reactor from the viewpoints of reducing time for maintenance and increasing productivity.

(Carbon Dioxide)

In this invention, carbon dioxide means gas containing a simple substance of carbon dioxide or carbon dioxide for 99.9% or more unless otherwise specified. Carbon dioxide is used as the diluent gas of the hydrofluorocarbon represented by the formula (1) in the step (I).

Carbon dioxide may be added in the step (I), or carbon dioxide which is generated as a by-product in a process manufacturing hydrofluoroolefin may be used as a whole or a part of the diluent gas in the step (I). It is preferable to add carbon dioxide because an amount of the diluent gas in the step (I) can be adjusted.

As carbon dioxide to be added, gaseous carbon dioxide (hereinafter, it is also referred to as carbon dioxide gas) may be used independently, or mixed gas containing the carbon dioxide gas, oxygen, nitrogen, helium, argon, carbon tetrachloride, and so on at an arbitrary ratio may be used.

Other compounds are compounds other than the hydrofluorocarbon represented by the formula (1), carbon dioxide, and the hydrofluoroolefin represented by the formula (2). As other compounds, there can be cited, for example, impurities derived from a manufacturing method or the like, diluent gas other than carbon dioxide, and so on.

As the impurities, there can be cited trifluoromethane (HFC-23), HFC-32, HFC-134, HFC-143a, HFO-1132a, trans-1,2-difluoroethylene (HFO-1132(E)), cis-1,2-difluoroethylene (HFO-1132(Z)), vinyl fluoride (HFO-1141), HFO-1234yf, methane, ethane, ethylene, propane, propylene, acetone, oxygen, fluorine, hydrogen fluoride, chlorine, hydrogen chloride, and so on.

As the diluent gas other than carbon dioxide, there can be cited nitrogen and carbon tetrachloride.

Regarding a content ratio of the hydrofluorocarbon represented by the formula (1) in the source gas in the step (I), it is preferable that a molar ratio between the hydrofluorocarbon represented by the formula (1) and carbon dioxide (hydrofluorocarbon/carbon dioxide) is 0.3/99.7 or more and 99.5/0.5 or less. The molar ratio is more preferably 5/95 or more and 70/30 or less from points of deterioration of the catalyst, a removal ratio of carbon dioxide, a cost of an alkaline solution, and so on, and the most preferably 5/95 or more and 50/50 or less.

When the hydrofluoroolefin represented by the formula (2) is contained in the source gas in the step (I), the hydrofluoroolefin represented by the formula (2) contained in the source gas becomes a factor setting off an inverse reaction of a reaction generating the hydrofluoroolefin represented by the formula (2) in a static reaction represented by the reaction formula (3). From such a viewpoint, the hydrofluoroolefin represented by the formula (2) is preferably not contained in the source gas. When the hydrofluoroolefin represented by the formula (2) is contained, a content ratio of the hydrofluoroolefin in the source gas is preferably 0.001 mol % or more and 20 mol % or less, more preferably 0.001 mol % or more and 10 mol % or less, and the most preferably 0.001 mol % or more and 5 mol % or less.

Other compounds in the source gas are preferably not contained from a viewpoint of suppressing an unnecessary side reaction resulting from deterioration of the catalyst and a viewpoint of reducing a load of a refining process of hydrofluoroolefin performed thereafter by suppressing generation of unnecessary by-products. When other compounds are contained in the source gas, an amount is preferably 0.001 mol % or more and 10 mol % or less, more preferably 0.001 mol % or more and 5 mol % or less, and the most preferably 0.001 mol % or more and 1 mol % or less.

(Catalyst)

The catalyst used in the step (I) has a catalytic action for the dehydrofluorination reaction of the hydrofluorocarbon represented by the formula (1). As the catalyst, there can be cited metal element, metal oxide, metal halide, and so on. Among these substances, the metal oxide or the metal halide is preferable because the hydrofluorocarbon represented by the formula (1) can be efficiently converted into the hydrofluoroolefin represented by the formula (2). One kind of the catalyst may be used independently, or two or more kinds may be used together.

As metal forming the metal element, the metal oxide, and the metal halide, there can be cited a transition metal element, a group 12 metal element, a group 13 metal element, and metal silicon. Among them, a group 6 metal element, a group 8 metal element, a group 10 metal element, the group 12 metal element, and the group 13 metal element are preferable, and chromium, iron, zinc, aluminum are more preferable.

The metal element may be one kind of the above-stated metals, or an alloy of two or more kinds of the metals.

The metal oxide may be one kind of oxide of the above-stated metals, or a composite oxide of two or more kinds of the metals.

The metal halide may be one kind of halide of the above-stated metals, or a composite halide of two or more kinds of the metals.

As the catalyst, specifically, there can be cited cobalt, nickel, palladium, chromium oxide, aluminum oxide, zinc oxide, iron fluoride, aluminum fluoride, aluminum chloride, chromium fluoride, chromium chloride, silicon oxide, and so on. Silica gel is preferable as the silicon oxide. Among them, the aluminum oxide, the aluminum fluoride and the chromium oxide are preferable from a point where the hydrofluorocarbon represented by the formula (1) can be efficiently converted into the hydrofluoroolefin represented by the formula (2).

A specific surface area of the catalyst measured by a BET method (hereinafter, it is referred to as a BET specific surface area) is preferably 50 m$^2$/g or more and 400 m$^2$/g or less, and more preferably 200 m$^2$/g or more and 400 m$^2$/g or less. When the BET specific surface area of the catalyst is in the above-stated range, the hydrofluorocarbon represented by the formula (1) reacts at a high reaction rate, and therefore, the catalyst is difficult to be scattered and has good handleability because a density of particles of the catalyst is not too small in addition that reaction efficiency is good.

The catalyst may be supported by a carrier. As the carrier, there can be cited, for example, an alumina carrier, a zirconia carrier, a silica carrier, a silica-alumina carrier, a carbon carrier typified by activated carbon, a barium sulfate carrier, a calcium carbonate carrier, and so on. As the activated carbon, there can be cited, for example, the activated carbon prepared from raw materials such as wood, charcoal, fruit shell, palm shell, peat, lignite, coal, and so on.

The catalyst is preferably activation treated beforehand from a viewpoint of improving a conversion ratio. As a method of the activation treatment, there can be cited a method where the catalyst is brought into contact with an activation treatment agent while being heated or not heated. As the activation treatment agent, there can be cited, for example, oxygen, hydrogen fluoride, hydrogen chloride, a fluorine-containing compound, and so on, and among them, the fluorine-containing compound is preferable. As the fluorine-containing compound, there can be cited, for example, HFC-143, HFC-143a, HFC-134, HFC-134a, HFC-245cb, HFC-245eb, HFC-245fa, HFO-1132a, HFO-1132(E), HFO-1132(Z), HFO-1123, HFO-1234yf, HFO-1234ze, trichlorofluoromethane (HFC-11), dichlorofluoromethane (HFC-21), chlorodifluoromethane (HFC-22), HFC-32, tetrafluoroethylene (FO-14), HFC-125, and so on. Note that products obtained in the step (I) are excluded from among these activation treatment agents.

It is preferable to carry out a reactivation treatment for the catalyst in addition to the activation treatment before the reaction. That is, it is preferable to carry out the reactivation treatment for the catalyst when the activity of the catalyst is lowered in the conversion reaction, and the conversion ratio of the hydrofluorocarbon represented by the formula (1) being the raw material component and selectivity of the hydrofluoroolefin represented by the formula (2) being the object are lowered. It is preferable to reproduce the activity of the catalyst by the reactivation treatment to reuse the catalyst.

As a method of the reactivation treatment, there can be cited a method where the catalyst after usage is brought into contact with the reactivation treatment agent while being heated or not heated similar to the activation treatment which is carried out before usage. As the reactivation treatment agent, there can be used oxygen, hydrogen fluoride, hydrogen chloride, a fluorine-containing compound, and so on. As the fluorine-containing compound, there can be cited, for example, HFC-143, HFC-143a, HFC-134, HFC-134a, HFC-245cb, HFC-245eb, HFC-245fa, HFO-1132a, HFO-1132(E), HFO-1132(Z), HFO-1123, HFO-1234yf, HFO-1234ze, HFC-11, HFC-21, HFC-22, HFC-32, FO-14, HFC-125, and so on. Note that products obtained in the step (I) are excluded from these reactivation treatment agents.

Note that it is preferable to use inert gas such as nitrogen, argon, helium to dilute the activation treatment agent from points of suppressing a side reaction, improving durability of the catalyst, and so on.

(Contact Between Source Gas and Catalyst)

When the source gas and the catalyst are brought into contact in the step (I), the catalyst may be in contact with the source gas in a solid state (solid phase) or in a state dispersed in a liquid medium capable of dispersing the catalyst (liquid phase). As the liquid medium dispersing the catalyst, there can be cited, for example, water, alcohol such as methanol and ethanol, a chlorine solvent such as carbon tetrachloride, N,N-dimethylformamide, N,N-dimethylacetamide, dimethylsulfoxide, tetraethyleneglycoldimethylether, triethyleneglycoldimethylether, diethyleneglycoldimethylether, propylene glycol monomethyl ether monoacetate, and so on. When the source gas is brought into contact with the catalyst which is in the state dispersed in the liquid medium, a pressure of the source gas becomes high and the reaction at a high temperature is difficult, and therefore, it is preferable that the catalyst in the solid phase is brought into contact with the source gas.

Hereinafter, regarding the step (I), there is described a mode where the source gas in a gas phase which is continuously supplied to the reactor is brought into contact with the catalyst in the solid phase which is input to the reactor by batch, but the step (I) in the manufacturing method of hydrofluoroolefin of this invention is not limited to the mode.

In the embodiment where the source gas in the gas phase and the catalyst in the solid phase are continuously brought into contact to be reacted, it is preferable to control content ratios of the hydrofluorocarbon represented by the formula (1) in the source gas and the diluent gas by controlling flow rates of respective gas phase components of the source gas and the diluent gas per a unit time.

(Reactor and Reaction Conditions)

As the reactor where the source gas and the catalyst are brought into contact to be reacted in the step (I), a shape and a structure thereof are not particularly limited as long as it is capable of sustaining later-described temperature and pressure. For example, a cylindrical vertical reactor can be cited. As a material of the reactor, there can be cited glass, iron, nickel, an alloy whose main component is iron or nickel, and so on. The reactor may include a heating unit such as an electric heater heating in the reactor.

The catalyst in the solid phase which is input to the reactor may be accommodated in either form of a fixed bed type or a fluidized bed type. In case of the fixed bed type, either a horizontal fixed bed type or a vertical fixed bed type is available. When the source gas is mixed gas composed of multiple components, it is preferable that the reactor is the vertical fixed bed type because occurrence of concentration distribution of each component due to a specific gravity difference is easy to be prevented.

The source gas may be supplied to the reactor at room temperature, but the source gas is preferably heated (pre-heating) before it is supplied to the reactor, and then supplied so as to increase reactivity in the reactor. When the preheating of the source gas is performed, it is preferable that the source gas is supplied to the reactor after it is heated to a temperature of 50° C. or more and 400° C. or less.

The source gas supplied to the reactor is brought into contact with the catalyst in the solid phase in the reactor. The temperature of the source gas in the reactor is preferably 200° C. or more and 1200° C. or less from viewpoints of improving reactivity and operating life of the catalyst. Further, the temperature of the source gas in the reactor is more preferably 300° C. or more and 1000° C. or less from viewpoints of reaction efficiency, suppression of a side-reaction and production equipment. Besides, the pressure in the reactor is preferably not a pressure around a critical point but specifically a gauge pressure of −0.1 MPa or more and 2.0 MPa or less and more preferably −0.1 MPa or more and 0.5 MPa or less. A contact time between the source gas and the catalyst in the reactor is preferably 0.1 seconds or more and 500 seconds or less, more preferably 0.5 seconds or more and 50 seconds or less, and particularly preferably 5 seconds or more and 30 seconds or less.

(First Gas Composition)

In the step (I), it is possible to obtain the first gas composition containing the hydrofluoroolefin represented by the formula (2), carbon dioxide, and the hydrofluorocarbon represented by the formula (1) which is unreacted as outlet gas of the reactor. The first gas composition may contain the other compounds in the step (I) and the other components being the by-products generated in the step (I) in addition to the hydrofluoroolefin represented by the formula (2) being the object, carbon dioxide, and the unreacted hydrofluorocarbon represented by the formula (1). As the other components contained in the first gas composition, there can be cited, for example, HFO-1141, HFO-1132a, HFO-1132(Z), HFO-1132(E), HFC-134, HFC-143, HFC-134a, HFC-125, HFC-23, HFC-32, methane, ethylene, ethane, propylene, propane, and so on when the hydrofluorocarbon represented by the formula (1) is HFC-134a and the hydrofluoroolefin represented by the formula (2) is HFO-1123.

<Step (II)>

In the step (II), carbon dioxide is separated from the first gas composition to obtain the second gas composition where a content ratio of hydrofluoroolefin is increased. As a method separating carbon dioxide, it is not particularly limited, and can be arbitrary selected according to reaction conditions and reaction products. For example, there can be cited a chemical absorption method where carbon dioxide is absorbed by an alkaline solution, a physical absorption method where carbon dioxide is physically dissolved in an absorbing liquid under high-pressure and low-temperature, an adsorption separation method where carbon dioxide is adsorbed by a porous adsorbent, a membrane separation method where carbon dioxide is separated by being passed through a separation membrane, a separation method where carbon dioxide is made into a solid state under high-pressure and low-temperature, and so on. Among these methods, a single method may be used or a plurality of methods may be combined. When a single method is carried out, the reaction may be one-step reaction or a several-step reaction by dividing into several steps. As the method separating carbon dioxide, the chemical absorption method where carbon dioxide is absorbed by the alkaline solution is preferable. Note that there is a case when hydrogen fluoride is also separated in addition to carbon dioxide depending on the separation method.

When carbon dioxide is separated by the chemical absorption method, the alkaline solution used in the step (II) is not particularly limited as long as it is possible to separate carbon dioxide contained in the first gas composition, and it is arbitrary selected according to the reaction conditions and the reaction products. At this time, carbon dioxide contained in the first gas composition can be separated from hydrofluoroolefin by bringing the first gas composition into contact with the alkaline solution. The alkaline solution preferably contains an inorganic base or an organic base where pKa of conjugate acid is six or more, and more preferably contains the inorganic base or the organic base where pKa of conjugate acid is nine or more. One kind of the inorganic base or the organic base contained in the alkaline solution may be used independently, or two or more kinds may be combined to be used. The pKa is an acidity of the conjugate acid of the base in water. As the alkaline solution, an alkaline aqueous solution is preferable.

As the inorganic base, there can be cited alkali metal alkoxide, alkaline earth metal alkoxide, tetraalkylammonium hydroxide, alkali metal hydroxide, alkaline earth metal hydroxide, and so on. As the inorganic base, sodium hydroxide, potassium hydroxide, magnesium hydroxide, calcium hydroxide, sodium oxide, potassium oxide, magnesium oxide, calcium oxide, lithium hydroxide, potassium hydrogen carbonate, potassium carbonate, sodium carbonate, sodium hydrogen carbonate, magnesium hydrogen carbonate, magnesium carbonate, calcium hydrogen carbonate, and calcium carbonate are preferable, and the sodium hydroxide, the potassium hydroxide, the calcium oxide, and the potassium carbonate are more preferable from a viewpoint of cost.

As the organic base, there can be cited alkylamines, alkanolamines, polyamines, cyclic amines, amino acids, aminosulfonic acids and salts of them, and so on.

As the alkylamines, trialkylamine is preferable. As trialkylamine, there can be cited methyldiethylamine, triethylamine, tripropylamine, tributylamine, and so on.

As the alkanolamines, monoalkanolamine, dialkanolamine, and trialkanolamine are preferable. As monoalkanolamine, there can be cited monomethanolamine, monoethanolamine, n-propanolamine, isopropanolamine, 2-methylaminoethanol, 2-ethylaminoethanol, 2-propylaminoethanol, 2-amino-2-methyl-1-propanol, 2-isopropylaminoethanol, 3-piperidinemethanol, 3-quinuclidinol, 2-dimethylaminoethanol, and 2-diethylaminoethanol. As dialkanolamine, there can be cited diethanolamine, N-methyldiethanolamine, diglycolamine, diisopropanolamine, and 3-piperidino-1,2-propanediol. As trialkanolamine, there can be cited triethanolamine.

As the polyamines, xylylenediamine, ethylenediamine, triethylenediamine, and diethylenetriamine are preferable.

As the cyclic amines, piperadine, piperidine, and pyrrolidine are preferable.

As the amine acids, α-amino acid and β-amino acid are preferable. As α-amino acid, there can be cited N,N-dimethylglycine, N-methylalanine, and 2-methylalanine. As β-amine acid, there can be cited β-alanine, 3-methylaminopropionic acid, and iminodipropionic acid.

As the aminosulfonic acids, α-aminosulfonic acid and β-aminosulfonic acid are preferable. As α-aminosulfonic acid, there can be cited aminomethanesulfonic acid. As β-aminosulfonic acid, there can be cited 2-aminoethanesulfonic acid and 2-(methylamino)ethanesulfonic acid.

As the organic base, triethylamine, tributylamine, monoethanolamine, n-propanolamine, and N-methyldiethanolamine are more preferable, and triethylamine, monoethanolamine, n-propanolamine, and N-methyldiethanolamine are the most preferable from a viewpoint of cost.

A concentration of the alkaline solution is preferably 5 mass % or more and 60 mass % or less, and more preferably 10 mass % or more and 60 mass % or less. A temperature of the alkaline solution is preferably 5° C. or more and 60° C. or less.

The alkaline solution may contain phosphoric acid-based anticorrosive or the like, silicone-based defoaming agent or the like, antioxidant, absorption promoter, and so on.

When carbon dioxide is separated by the physical absorption method, the absorbing liquid used in the step (II) is not particularly limited as long as carbon dioxide contained in the first gas composition can be separated, and it is arbitrary selected according to the reaction conditions and the reaction products. As the absorbing liquid, there can be cited methanol, polyethyleneglycol, glyme, sulfolane, and ionic liquid (a combination of $[R,R'-N_2C_3H_3]^+$ and $[R-NC_5H_5]^+$, a combination of $PF_6^-$ and $BF_4^-$, and so on). One kind of the absorbing liquid may be used independently, or two or more kinds may be used together.

When carbon dioxide is separated by the adsorption separation method, the adsorbent used in the step (II) is not particularly limited as long as carbon dioxide contained in the first gas composition can be separated, and it is arbitrary selected according to the reaction conditions and the reaction products. As the adsorbent, there can be cited a porous body such as zeolite and activated carbon, and so on. One kind of adsorbent may be used independently, or two or more kinds may be used together.

When carbon dioxide is separated by the membrane separation method, the separation membrane used in the step (II) is not particularly limited as long as carbon dioxide contained in the first gas composition can be separated, and it is arbitrary selected according to the reaction conditions and the reaction products. As the separation membrane, there can be cited a polymer membrane such as polyamidoamine dendrimer, a ceramic membrane, a carbon membrane, an impregnated liquid membrane, and so on. One kind of the separation membrane may be used independently, or two or more kinds may be used together.

(Recovery Method of Carbon Dioxide)

It is possible to recover carbon dioxide separated in the step (II). The recovery methods are different depending on the separation methods of carbon dioxide. For example, there can be cited a method to recover carbon dioxide by heating the absorbing liquid such as the alkaline solution to let carbon dioxide release in case of the chemical absorption method, a method to recover carbon dioxide by reducing a pressure and heating the absorbing liquid to let carbon dioxide diffuse in case of the physical absorption method, a method to recover carbon dioxide by setting the adsorbent under low-pressure to let carbon dioxide desorb in case of the adsorption separation method, and so on. The recovered carbon dioxide can be reused again as the diluent gas of the step (I).

(Second Gas Composition)

In the step (II), it is possible to obtain the second gas composition containing the hydrofluoroolefin represented by the formula (2) and the unreacted hydrofluorocarbon represented by the formula (1). The second gas composition may contain compounds and components which are the same as the other compounds and the other components in the step (I) in addition to the hydrofluoroolefin represented by the formula (2) being the object and the unreacted hydrofluorocarbon represented by the formula (1). In the step (II), carbon dioxide contained in the first gas composition is selectively separated, and thereby, the content ratio of hydrofluoroolefin in the second gas composition becomes higher than the content ratio of hydrofluoroolefin in the first gas composition.

The second gas composition is able to be used for various uses as it is, and it is preferably further refined. As a refining method, there can be cited publicly known methods such as distillation, adsorption, washing with an acid aqueous solution, a basic aqueous solution or a neutral aqueous solution. Substances other than the hydrofluoroolefin represented by the formula (2) contained in the second gas composition are able to be removed and separated to a desired degree by publicly known methods. The preferable refining method is the method to distillate under an atmospheric pressure, an added pressure, or a reduced pressure. It is possible to obtain high-purity hydrofluoroolefin by carrying out the distillation under such a pressure. Besides, the unreacted hydrofluorocarbon represented by the formula (1) separated from the second gas composition can be recycled as a part of the source gas in the step (I).

<Step (A)>

Further, the manufacturing method of hydrofluoroolefin of this invention preferably includes the step (A) to separate hydrogen fluoride contained in the first gas composition between the step (I) and the step (II). When the step (A) is included, an amount of hydrogen fluoride separated in the step (II) becomes very small compared to an amount of hydrogen fluoride separated in the step (A).

The first gas composition may be supplied at the step (A) as it is, or may be supplied at the step (A) after performing other processes for the first gas composition by providing said other process steps between the step (I) and the step (A). Here, other processes means the processes other than the separations of hydrogen fluoride and carbon dioxide, and not changing compositions of substances other than water contained in the first gas composition. As other processes, there can be cited, for example, storing to a tank, compression by a compressor, heating, cooling, removal of water, and so on.

As the method to separate hydrogen fluoride from the first gas composition, there can be cited methods such as distillation, adsorption, and a two-phase separation.

The distillation is a method to separate hydrogen fluoride by distilling the first gas composition. The distillation can be carried out under the atmospheric pressure, the added pressure or the reduced pressure, but it is preferably carried out under the added pressure from a viewpoint of improving separation efficiency.

The adsorption is a method to bring the first gas composition into contact with an adsorbent so as to adsorb hydrogen fluoride by the adsorbent to be separated. The adsorbent may be in a solid phase, or may be in a state dispersed in a liquid medium where the adsorbent is not dissolved (liquid phase). As the adsorbent, sodium fluoride, potassium fluoride, zeolite, activated carbon, and so on can be used. Among them, sodium fluoride is particularly preferable because hydrogen fluoride can be efficiently separated.

The two-phase separation is a method where the first gas composition is made into a liquid phase under an added pressure to be separated into two phases of an organic phase containing the hydrofluoroolefin represented by the formula (2), carbon dioxide, and the hydrofluorocarbon represented by the formula (1) and an acid phase containing hydrogen fluoride, to separate the phase-separated acid phase.

It is possible to obtain a gas composition whose content ratio of hydrogen fluoride is lower than the first gas composition by performing the step (A) where the separation process of hydrogen fluoride is carried out. That is, it is possible to obtain the gas composition whose content ratio of hydrogen fluoride is low and which contains the hydrofluoroolefin represented by the formula (2), carbon dioxide, and the unreacted hydrofluorocarbon represented by the formula (1) by performing the step (A). When the manufacturing method of hydrofluoroolefin of this invention includes the step (A), it is possible to use the gas composition as the first gas composition. In the gas composition obtained by the step (A), there is a case when a content ratio of acidic components such as hydrogen chloride and carbon dioxide and a content ratio of compounds other than the acidic components contained in the other compounds and the other components are lower than those of the first gas composition. When carbon dioxide is separated in the step (A), an amount of carbon dioxide separated in the step (A) is very small compared to an amount of carbon dioxide separated in the step (II).

Note that the gas composition obtained by the step (A) may be supplied at the step (II) as it is, or may be supplied at the step (II) after performing other processes for the gas composition by providing said other process steps between the step (A) and the step (II). Here, other processes means the processes other than the separation of carbon dioxide, and not changing compositions of substances other than water contained in the gas composition. As other processes, there can be cited, for example, storing to a tank, compression by a compressor, heating, cooling, removal of water, and so on.

<Reaction Device>

The FIGURE is a schematic view illustrating an example of a reaction device used for the manufacturing method of hydrofluoroolefin of this invention. A reaction device 1 includes a reactor 2 having a heating unit such as an electric heater to carry out the step (I) and a carbon dioxide trap 3 to carry out the step (II). Note that in the reactor 2, the heating unit is not necessarily provided. Besides, a hydrogen fluoride trap 4 may be included according to need to carry out the step (A) between the step (I) and the step (II). In the FIGURE, there is described a mode where the chemical absorption method using the alkaline solution is used, but the separation method of carbon dioxide in the manufacturing method of hydrofluoroolefin of this invention is not limited to the mode as stated above.

A catalyst 5 is accommodated in the reactor 2 to form the vertical fixed bed. Besides, an upper part being an inlet side of the reactor 2 is connected to a preheating mixer 6 which includes a heating unit such as an electric heater through a source gas supply line 7. It is preferable that the heating unit such as the electric heater is provided also at the source gas supply line 7.

Note that in the reactor 2, the source gas may be supplied from the upper part toward a lower part of the heater 2, or the source gas may be supplied from the lower part toward the upper part of the reactor 2.

A hydrofluorocarbon supply line 8 which supplies the hydrofluorocarbon represented by the formula (1) and a carbon dioxide supply line 9 which supplies carbon dioxide being the diluent gas are each connected to the preheating mixer 6. The hydrofluorocarbon represented by the formula (1) and carbon dioxide are respectively introduced into the preheating mixer 6 through the hydrofluorocarbon supply line 8 and the carbon dioxide supply line 9, mixed and heated to a predetermined temperature in the preheating mixer 6, and then, supplied to the reactor 2 through the source gas supply line 7. The hydrofluorocarbon supplied to the reactor 2 is brought into contact with the catalyst 5 in the presence of carbon dioxide to be converted into the hydrofluoroolefin represented by the formula (2). As a result, the first gas composition containing the hydrofluoroolefin represented by the formula (2), carbon dioxide, hydrogen fluoride, and the unreacted hydrofluorocarbon represented by the formula (1) is obtained.

Note that the hydrofluorocarbon supply line 8 and the carbon dioxide supply line 9 may be coupled before they are connected to the preheating mixer 6, to mix the hydrofluorocarbon represented by the formula (1) and carbon dioxide beforehand, then the mixed resultant is supplied to the preheating mixer 6. Besides, at least one of the hydrofluorocarbon supply line 8 and the carbon dioxide supply line 9 may be equipped with a preheater including an electric heater or the like, and the hydrofluorocarbon represented by the formula (1) and carbon dioxide are supplied to the preheating mixer 6 after preheating at least one of the hydrofluorocarbon represented by the formula (1) and carbon dioxide which is supplied through the line equipped with the preheater.

The lower part of the reactor 2 being an outlet side is connected to the hydrogen fluorine trap 4 where the adsorbent adsorbing hydrogen fluorine is filled, through a reactor outlet line 10 which includes a heating unit such as an electric heater. The first gas composition obtained at the reactor 2 is supplied to the hydrogen fluoride trap 4, and the hydrogen fluoride contained in the first gas composition is adsorbed by the adsorbent by passing through the hydrogen fluoride trap 4 where the adsorbent is filled. As a result, the first gas composition from which hydrogen fluoride is removed is obtained.

An outlet of the hydrogen fluoride trap 4 is connected to the carbon dioxide trap 3 where the alkaline solution is accommodated, through an outlet line 11. The first gas composition passing through the hydrogen fluoride trap 4 is supplied to the carbon dioxide trap 3, bubbled in the alkaline solution, whereby carbon dioxide contained in the first gas composition reacts with the alkaline solution. Carbon dioxide contained in the first gas composition is thereby separated, and the second gas composition containing the hydrofluoroolefin represented by the formula (2) is obtained.

An outlet of the carbon dioxide trap 3 is connected to a dehydrator 13 through an outlet line 12. The second gas composition obtained at the carbon dioxide trap 3 is supplied to the dehydrator 13, and water contained in the second gas composition is removed. The second gas composition from which water is removed by the dehydrator 13 is collected into a sampling bag 14, and thereafter, a component of the second gas composition is analyzed by an analyzer 15 such as a gas chromatography (GC).

According to the manufacturing method of hydrofluoroolefin of this invention, it is possible to easily separate hydrofluoroolefin and carbon dioxide being the diluent gas even when the boiling point of hydrofluoroolefin is low. As a result, it is possible to suppress the manufacturing cost and to increase the productivity of hydrofluoroolefin.

Hydrofluoroolefins manufactured by the manufacturing method of this invention, for example, HFO-1123 and HFO-1234yf are useful as a refrigerant taking over HFC-32 or HFC-125 being the greenhouse effect gas, and as a raw material monomer of a functional material such as a piezoelectric element and film, and as a synthesis intermediate.

EXAMPLES

Hereinafter, the present invention is described in detail by using examples, but the present invention is not limited to the following examples.

<Reaction Device>

In examples and comparative examples, the reaction device illustrated in the FIGURE (hereinafter, it is denoted as a reaction device (1)) was used.

(Reaction Device (1))

In the reaction device (1), a vertical fixed bed reactor manufactured by SUS316L (JIS standard) with 22.66 mm in inside diameter×300 mm in height was used as the reactor 2. In the reactor 2, the catalyst 5 illustrated in each of the examples and comparative examples was filled at a height of 100 mm. Besides, an inside of the reactor 2 was heated by an electric furnace.

The source gas supply line 7 connected to the reactor 2 at the inlet side was heated to be in a range of 100° C. or more and 120° C. or less by a ribbon heater. It was constituted such that HFC-134a being the hydrofluorocarbon represented by the formula (1) and carbon dioxide being the diluent gas were each adjusted in flow rate by a mass flow controller (not-illustrated) provided at each of the hydrofluorocarbon supply line 8 and the carbon dioxide supply line 9 to be mixed, and then supplied to the preheating mixer 6.

The reactor outlet line 10 connected to the reactor 2 at the outlet side was heated to be in a range of 100° C. or more and 120° C. or less by a ribbon heater, and connected to the hydrogen fluoride trap 4 where 30 g of 1/16 inch sodium fluoride pellet was filled. The outlet line 11 which was connected to the hydrogen fluoride trap 4 at the outlet side was connected to the carbon dioxide trap 3 which accommodates 20 mass % potassium hydroxide aqueous solution. The outlet line 12 which was connected to the carbon dioxide trap 3 at the outlet side was connected to the dehydrator 13 where 120 g of molecular sieves 3A in a pellet state (manufactured by Junsei Chemical Co., Ltd., 1/8 inch pellet) were filled. Besides, it was constituted such that the second gas composition passing through the dehydrator 13 was collected by the sampling bag 14 which was made of polyvinylidene fluoride (PVdF) connected to the dehydrator 13, and thereafter, composition analysis of the second gas composition was carried out with the analyzer 15.

<Analysis Conditions>

In the analyzer 15, the GC was used for the composition analysis of the second gas composition. As a column, DB-1 (manufactured by Agilent Technologies Co., Ltd., 60 m in length×250 μm in inside diameter×1 μm in thickness) was used. As a detector, FID was used.

<Linear Velocity>

A linear velocity means a superficial velocity, and it was calculated by assuming that the reactor which let the source gas through was an empty tower where filling materials were not filled therein, and dividing a flow rate (volume flow rate) by a cross-sectional area of the reactor being the empty tower. Note that experiments were performed by setting this linear velocity at 1 cm/s.

Linear velocity (superficial velocity) (cm/s)= flow rate (cm$^3$/s)/cross-sectional area (cm$^2$)

Example 1

The reactor 2 of the reaction device (1) was filled with 40 g of alumina catalyst (manufactured by JGC C&C, brand name: ACBM-1, shape: spherical shape with a particle size of 2 mm), then it was heated at 350° C. for 48 hours while supplying nitrogen gas at 300 mL/min to be dried.

Next, a temperature in the reactor 2 was set to 350° C., and mixed gas where 5 mol % HFC-134a and 95 mol % nitrogen were mixed was supplied to the reactor 2 at the linear velocity of 1 cm/s. HFC-134a and nitrogen were continuously passed through, then it was verified that a composition of outlet gas which had passed through the hydrogen fluoride trap 4 where sodium fluoride pellet was filled became stable after four hours.

Next, the temperature in the reactor 2 was set to 350° C., and source gas where 5 mol % HFC-134a and 95 mol % carbon dioxide as diluent gas were mixed was supplied to the reactor 2. HFC-134a and carbon dioxide were continuously passed through, then it was verified that a composition of outlet gas which had passed through the hydrogen fluoride trap 4 (hereinafter, it is referred to as NaF passing outlet gas) became stable. Next, the NaF passing outlet gas was supplied to the carbon dioxide trap 3 and the dehydrator 13, after a composition of outlet gas which had passed through the carbon dioxide trap 3 and the dehydrator 13 (hereinafter, it is referred to as KOH passing outlet gas) became stable, a sample of the KOH passing outlet gas was collected every two hours. An alkaline aqueous solution in the carbon dioxide trap 3 was stirred with a stirring bar. At this time, the first gas composition which had passed through the carbon dioxide trap 3 formed fine air bubbles in the alkaline aqueous solution. Note that a room temperature at the sample collecting time was 25° C.

A conversion ratio of HFC-134a and selectivity of HFO-1123 were each found as described below based on a molar ratio (mol %) of each component in the KOH passing outlet gas which was obtained by the analysis of GC.

In the following expression used in the calculation, (HFC-134a)$_{in}$, (HFC-134a)$_{out}$, (HFO-1123)$_{out}$ and (total)$_{out}$ respectively represent GC areas of HFC-134a in the source gas, HFC-134a and HFO-1123 in the KOH passing outlet gas except the diluent gas, and total KHO passing outlet gas components. Note that carbon dioxide and air are excluded because they are not detected. Incidentally, in this example, the calculation was performed while assuming that (HFC-134a)$_{in}$=(total)$_{out}$.

Note that the molar ratio of each component in the KOH passing outlet gas was calculated by multiplying an area ratio of each component identified by GC by a detection sensitivity factor measured by using a reference material whose composition ratio is already known. Besides, the molar ratio between HFC-134a and carbon dioxide in the source gas was calculated from a flow rate ratio between HFC-134a and carbon dioxide.

[Conversion Ratio of HFC-134a (Mol %)]

The conversion ratio of HFC-134a means a ratio of HFC-134a which is converted into other components including HFO-1123 and consumed due to the reaction. The conversion ratio of HFC-134a is calculated by the following expression.

Conversion ratio of HFC-134a (mol %)={1−(HFC-134a)$_{out}$/(HFC-134a)$_{in}$}×100

[Selectivity of HFO-1123 (mol %)]

The selectivity of HFO-1123 means a ratio converted into HFO-1123 among the reacted HFC-134a. The selectivity of HFO-1123 is calculated by the following expression.

Selectivity of HFO-1123 (mol %)=(HFO-1123)$_{out}$/{1−(HFC-134a)$_{out}$/(HFC-134a)$_{in}$}×100

Note that these results were each an average value of analyses of samples which were collected from after the reaction became stable until the reaction finished.

Calculation results of the conversion ratio of HFC-134a and the selectivity of HFO-1123 are illustrated in Table 1 together with reaction conditions (HFC-134a flow rate (mol %), carbon dioxide flow rate (mol %) which are supplied to the reactor, temperature in the reactor (° C.)).

Note that the temperature in the reactor is the temperature in the reactor 2, and it is an actual measured value. Besides, the linear velocity is the linear velocity of the source gas supplied to the reactor.

Examples 2 to 10

The reactions were continuously carried out similar to the example 1 except that the reaction conditions were changed as illustrated in Table 1. The conversion ratio of HFC-134a and the selectivity of HFO-1123 were found similar to the example 1. Obtained results are illustrated in Table 1.

Examples 11, 12

The reactions were continuously carried out similar to the example 1 except that the reactor 2 of the reaction device (1) was filled with 40 g of aluminum trifluoride (manufactured by Kanto Chemical Co., Inc., brand name: Aluminum Trifluoride, shape: powder) as the catalyst, and the reaction conditions were changed as illustrated in Table 2. The conversion ratio of HFC-134a and the selectivity of HFO-1123 were each found similar to the example 1. Obtained results are illustrated in Table 2.

Example 13

The reactions were continuously carried out similar to the example 1 except that the composition of the source gas and the reaction conditions were changed as illustrated in Table 3. The conversion ratio of HFC-245eb and the selectivity of HFO-1234yf were calculated based on the following expression.

In the following expression used in the calculation, (HFC-245eb)$_{in}$, (HFC-245eb)$_{out}$, (HFO-1234yf)$_{out}$ and (total)$_{out}$ respectively represent GC areas of HFC-245eb in the source gas, HFC-245eb and HFO-1234yf in the KOH passing outlet gas except the diluent gas, and total KHO passing outlet gas components. Note that carbon dioxide and air are excluded because they are not detected. Incidentally, in this example, the calculation is performed while assuming that (HFC-245eb)$_{in}$=(total)$_{out}$.

Obtained results are illustrated in Table 3.

Conversion ratio of HFC-245eb (mol %)={1−(HFC-245eb)$_{out}$/(HFC-245eb)$_{in}$}×100

Selectivity of HFO-1234yf (mol %)=(HFO-1234yf)$_{out}$/{1−(HFC-245eb)$_{out}$/(HFC-245eb)$_{in}$}×100

Example 14

The reactions were continuously carried out similar to the example 1 except that the composition of the source gas and the reaction conditions were changed as illustrated in Table 4. The conversion ratio of HFC-245cb and the selectivity of HFO-1234yf were calculated from the following expression.

In the following expression used in the calculation, (HFC-245cb)$_{in}$, (HFC-245cb)$_{out}$, (HFO-1234yf)$_{out}$ and (total)$_{out}$ respectively represent GC areas of HFC-245cb in the source gas, HFC-245cb and HFO-1234yf in the KOH passing outlet gas except the diluent gas, and total KHO passing outlet gas components. Note that carbon dioxide and air are excluded because they are not detected. Incidentally, in this example, the calculation is performed while assuming that (HFC-245cb)$_{in}$=(total)$_{out}$.

Obtained results are illustrated in Table 4.

Conversion ratio of HFC-245cb (mol %)={1−(HFC-245cb)$_{out}$/(HFC-245cb)$_{in}$}×100

Selectivity of HFO-1234yf (mol %)=(HFO-1234yf)$_{out}$/{1−(HFC-245cb)$_{out}$/(HFC-245cb)$_{in}$}×100

Comparative Examples 1 to 7

The reactions were continuously carried out similar to the example 1 except that the composition of the source gas and the reaction conditions were changed as illustrated in Table 5. The conversion ratio of HFC-134a and the selectivity of HFO-1123 were calculated as same as the example 1. Obtained results are illustrated in Table 5.

TABLE 1

| | Composition ratio HFC-134a:CO$_2$ | | | Conversion ratio | Selectivity |
|---|---|---|---|---|---|
| | HFC-134a (mol %) | CO$_2$ (mol %) | Temperature (° C.) | of HFC-134a (%) | of HFO-1123 (%) |
| Example 1 | 5 | 95 | 350 | 11.9 | 92.6 |
| Example 2 | 20 | 80 | 350 | 5.2 | 93.6 |
| Example 3 | 40 | 60 | 350 | 3.3 | 94.9 |
| Example 4 | 5 | 95 | 400 | 38.4 | 93.5 |
| Example 5 | 5 | 95 | 450 | 64.5 | 90.2 |
| Example 6 | 20 | 80 | 450 | 17.4 | 96.1 |
| Example 7 | 40 | 60 | 450 | 12.2 | 96.2 |
| Example 8 | 60 | 40 | 450 | 8.0 | 99.8 |
| Example 9 | 5 | 95 | 500 | 81.7 | 96.3 |
| Example 10 | 40 | 60 | 500 | 24.3 | 95.5 |

TABLE 2

| | Composition ratio HFC-134a:CO$_2$ | | | Conversion ratio | Selectivity |
|---|---|---|---|---|---|
| | HFC-134a (mol %) | CO$_2$ (mol %) | Temperature (° C.) | of HFC-134a (%) | of HFO-1123 (%) |
| Example 11 | 5 | 95 | 400 | 15.0 | 99.4 |
| Example 12 | 5 | 95 | 500 | 51.7 | 99.7 |

TABLE 3

| | Composition ratio HFC-245eb:$CO_2$ | | | Conversion ratio | Selectivity |
|---|---|---|---|---|---|
| | HFC-245eb (mol %) | $CO_2$ (mol %) | Temperature (° C.) | of HFC-245eb (%) | of HFO-1234yf (%) |
| Example 13 | 5 | 95 | 400 | 91.2 | 92.4 |

TABLE 4

| | Composition ratio HFC-245cb:$CO_2$ | | | Conversion ratio | Selectivity |
|---|---|---|---|---|---|
| | HFC-245cb (mol %) | $CO_2$ (mol %) | Temperature (° C.) | of HFC-245cb (%) | of HFO-1234yf (%) |
| Example 14 | 5 | 95 | 400 | 89.4 | 93.1 |

TABLE 5

| | Composition ratio HFC-134a:$N_2$ | | | Conversion ratio | Selectivity |
|---|---|---|---|---|---|
| | HFC-134a (mol %) | $N_2$ (mol %) | Temperature (° C.) | of HFC-134a (%) | of HFO-1123 (%) |
| Comp. Exam. 1 | 20 | 80 | 250 | 0.7 | 94.2 |
| Comp. Exam. 2 | 20 | 80 | 300 | 1.9 | 93.5 |
| Comp. Exam. 3 | 20 | 80 | 350 | 5.5 | 90.6 |
| Comp. Exam. 4 | 5 | 95 | 400 | 36.2 | 94.8 |
| Comp. Exam. 5 | 20 | 80 | 400 | 18.9 | 94.5 |
| Comp. Exam. 6 | 100 | 0 | 400 | 2.7 | 89.4 |
| Comp. Exam. 7 | 100 | 0 | 450 | 8.2 | 95.6 |

As it can be seen from Tables 1, 2 and Table 5, each of the examples 1 to 12 where carbon dioxide was used as the diluent gas had reactivities (conversion ratio, selectivity) as the same degree as the comparative examples 1 to 5 where nitrogen was used as the diluent gas. As it can be seen from Tables 1, 2 and Table 5, the conversion ratio of HFC-134a becomes high as the molar ratio of HFC-134a in the source gas becomes smaller or as the temperature in the reactor becomes higher.

Example 15

The reactor 2 of the reaction device (1) was filled with 40 g of alumina catalyst (manufactured by JGC C&C, brand name: ACBM-1, shape: spherical shape with a particle size of 2 mm), then it was heated at 350° C. for 48 hours while supplying nitrogen gas at 300 mL/min to be dried.

Next, a temperature in the reactor 2 was set to 350° C., and mixed gas where 5 mol % HFC-134a and 95 mol % nitrogen were mixed was supplied to the reactor 2 at the linear velocity of 1 cm/s. HFC-134a and nitrogen were continuously passed through, then it was verified that a composition of outlet gas which had passed through the hydrogen fluoride trap 4 where sodium fluoride pellet was filled became stable after four hours.

Next, the temperature in the reactor 2 was set to 450° C., and source gas where 5 mol % HFC-134a and 95 mol % carbon dioxide as diluent gas were mixed was supplied to the reactor 2. HFC-134a and carbon dioxide were continuously passed through, then samples of the NaF passing outlet gas were collected by using a sampling bag which was connected to the outlet line 11 after five hours since the composition of the NaF passing outlet gas became stable, and thereafter, composition analysis was performed by an analyzer (not-illustrated). Next, the NaF passing outlet gas was supplied to the carbon dioxide trap 3 and the dehydrator 13, and the sample of the KOH passing outlet gas was collected after five hours since the composition of the KOH passing outlet gas became stable. The alkaline aqueous solution in the carbon dioxide trap 3 was stirred with a stirring bar. At this time, the first gas composition which had passed through the carbon dioxide trap 3 formed fine air bubbles in the alkaline aqueous solution. Note that the room temperature at the sample collecting time was 25° C.

Amounts of carbon dioxide contained in samples of the NaF passing outlet gas and the KOH passing outlet gas each obtained from a peak area were evaluated by using a gas chromatography mass spectrometry. Results evaluated by the gas chromatography mass spectrometry are illustrated in Table 6. Note that a molar ratio of $CO_2$/HFO-1123 in Table 6 was found from a calibration curve which was calculated by using a reference sample. Note that as a column of the gas chromatography mass spectrometry, DB-1 (manufactured by Agilent Technologies Co., Ltd., 60 m in length×250 μm in inside diameter×1 μm in thickness) was used. As a detector, TCD was used.

TABLE 6

| | NaF passing outlet gas | | | KOH passing outlet gas | | | Removal ratio (%) |
|---|---|---|---|---|---|---|---|
| | $CO_2$ (area %) | HFO-1123 (area %) | $CO_2$/HFO-1123 (mol ratio) | $CO_2$ (area %) | HFO-1123 (area %) | $CO_2$/HFO-1123 (mol ratio) | |
| Example 15 | 46.2 | 2.6 | 55.5 | 0.5 | 0.8 | 1.9 | 97 |

It can be seen from Table 6 that 97% of carbon dioxide contained in the first gas composition can be separated by the alkaline aqueous solution.

According to the manufacturing method of this invention, it is possible to efficiently and stably manufacture hydrofluoroolefin with low boiling point which corresponds to hydrofluorocarbon with low boiling point. Besides, it is possible to easily separate carbon dioxide being diluent gas by using an alkaline solution being an inexpensive material, and therefore, it is useful as an industrial manufacturing method. Further, carbon dioxide which has an adverse affect on global environment is used as a raw material, and therefore, it can be said that it is a manufacturing method taking into account of global environment.

What is claimed is:
1. A method for manufacturing hydrofluoroolefin, comprising:
   converting hydrofluorocarbon into hydrofluoroolefin in the presence of carbon dioxide to obtain a first gas composition containing the hydrofluoroolefin and the carbon dioxide, wherein a molar amount of the carbon dioxide at a beginning of the converting is from 80% to 95% with respect to a total molar amount of the carbon dioxide and the hydrofluorocarbon, and a reaction temperature in the converting is from 400° C. to 500° C.;

separating hydrogen fluoride contained in the first gas composition therefrom; and separating the carbon dioxide contained in the first gas composition after separating hydrogen fluoride contained therein to obtain a second gas composition containing the hydrofluoroolefin, wherein the converting, the separating of hydrogen fluoride and the separating of the carbon dioxide are carried out continuously, and wherein the hydrofluorocarbon is 1,1,1,2-tetrafluoroethane and the hydrofluoroolefin is trifluoroethylene.

2. The method according to claim 1,
wherein the separating of the carbon dioxide comprises bringing the first gas composition into contact with an alkaline solution.

3. The method according to claim 2,
wherein the alkaline solution comprises an inorganic base or an organic base where pKa of conjugate acid is six or more.

4. The method according to claim 3,
wherein the inorganic base is at least one selected from a group consisting of sodium hydroxide, potassium hydroxide, potassium carbonate and calcium oxide.

5. The method according to claim 3,
wherein the organic base is at least one selected from a group consisting of triethylamine, tributylamine, monoethanolamine, n-propanolamine and N-methyldiethanolamine.

6. The method according to claim 1,
wherein the converting comprises bringing the hydrofluorocarbon into contact with a catalyst.

7. The method according to claim 6,
wherein the catalyst is at least one selected from a group consisting of metal, metal oxide and metal halide.

8. The method according to claim 6,
wherein the catalyst is at least one selected from a group consisting of cobalt, nickel, palladium, chromium oxide, aluminum oxide, zinc oxide, iron fluoride, aluminum fluoride, aluminum chloride, chromium fluoride, chromium chloride and silicon oxide.

9. The method according to claim 1, further comprising:
recovering the carbon dioxide separated from the first gas composition; and
reusing the recovered carbon dioxide for converting the hydrofluorocarbon into the hydrofluoroolefin.

10. The method according to claim 6,
wherein the catalyst comprises aluminum oxide.

* * * * *